United States Patent
Healy et al.

[19]

[11] Patent Number: 6,074,419
[45] Date of Patent: Jun. 13, 2000

[54] INDICIA FOR PROSTHETIC DEVICE

[75] Inventors: Steven J. Healy, Vadnais Heights; Richard F. Schroeder, Oakdale, both of Minn.

[73] Assignee: St. Jude Medical, Inc., St. Paul, Minn.

[21] Appl. No.: 08/775,821

[22] Filed: Dec. 31, 1996

[51] Int. Cl.[7] ............................................. A61F 2/24
[52] U.S. Cl. .................. 623/2.14; 623/2.13; 623/2.15; 623/2.16; 623/910
[58] Field of Search ............................. 623/1, 2, 11, 12, 623/13, 66, 900, 3, 2.12, 2.13–2.16, 910, 901

[56] References Cited

U.S. PATENT DOCUMENTS

| | | | |
|---|---|---|---|
| 3,548,418 | 12/1970 | Angell et al. | 623/2 |
| 3,805,301 | 4/1974 | Liebig | 3/1 |
| 4,041,931 | 8/1977 | Elliott et al. | 623/1 |
| 4,055,861 | 11/1977 | Carpientier et al. | 623/2 |
| 4,219,721 | 8/1980 | Kamen et al. | 219/121 |
| 4,532,659 | 8/1985 | Kaster | 623/2 |
| 4,586,504 | 5/1986 | de Medinaceli | 128/335.5 |
| 5,047,050 | 9/1991 | Arpesani | 623/1 |
| 5,201,880 | 4/1993 | Wright et al. | 623/2 |
| 5,314,473 | 5/1994 | Godin | 623/2 |
| 5,409,472 | 4/1995 | Rawlings et al. | 604/307 |
| 5,509,930 | 4/1996 | Love | 623/2 |
| 5,509,932 | 4/1996 | Keogh et al. | 623/11 |
| 5,662,704 | 9/1997 | Gross | 623/2 |
| 5,697,970 | 12/1997 | Schmitt et al. | 623/1 |
| 5,713,953 | 2/1998 | Vallana et al. | 623/2 |
| 5,800,531 | 9/1998 | Cosgrove et al. | 623/900 |
| 5,861,028 | 1/1999 | Angell | 623/2 |

FOREIGN PATENT DOCUMENTS

| | | |
|---|---|---|
| 0 495 417 A1 | 7/1992 | European Pat. Off. . |
| 0 508 473 A2 | 10/1992 | European Pat. Off. . |
| 0 699 423 A2 | 3/1996 | European Pat. Off. . |
| WO 93/15690 | 8/1993 | WIPO . |
| WO 94/04099 | 3/1994 | WIPO . |
| WO 96/40007 | 12/1996 | WIPO . |

OTHER PUBLICATIONS

Brochure by Baxter Edwards AG, entitled "Sub–Coronary Implantation and Trimming Technique", (1996).

*Primary Examiner*—Mickey Yu
*Assistant Examiner*—Tram A. Nguyen
*Attorney, Agent, or Firm*—Hallie A. Finucane, Esq.; Westman, Champlin & Kelly, P.A.

[57] ABSTRACT

A prosthetic stentless aortic tissue valve includes a substantially annular valve body having a leaflet carried therein for occluding blood flow therethrough. A root extends generally coaxially from the valve body. Visual marking are provided on the root and act as a sculpting guide for a surgeon during implantation of the prosthetic heart valve to sculpt portions of sinus areas of the root.

6 Claims, 8 Drawing Sheets

INDICIA FOR PROSTHETIC DEVICE

FIELD OF THE INVENTION

This invention relates generally to implantable bioprosthetic devices, and more particularly is directed to implantable products to repair or replace the valves of the heart.

BACKGROUND OF THE INVENTION

Prosthetic heart valves are used to replace diseased natural heart valves. Several categories of prosthetic heart valves are in existence. In prosthetic heart valves, one or more leaflets or occluders are carried within an annulus of the prosthesis and act as a valve to blood flow. The leaflet may be of a biological material or a synthetic material for bioprosthetics or, in a mechanical prosthesis, may be of a biocompatible material such as pyrolytic carbon.

One type of bioprosthetic heart valve is a stentless aortic tissue valve. Such tissue valves include a root version and a sub-coronary version. The root version includes an aortic root which is used to replace a diseased aortic root of a patient. However, in instances where the natural aortic root (or aortic arch) is healthy, the sub-coronary version may be used and the native root can be left intact.

In many instances, the surgeon will excise (or "sculpt") portions of the sinus areas of the prosthetic aortic root of the root version stentless aortic tissue valve to form a sub-coronary prosthesis. Often, this procedure must be done during surgery when operative time is limited. It is difficult to accurately sculpt the sinus areas and avoid damage to the leaflets due to lack of visibility of the inside of the heart valve. Currently, stentless aortic roots have been provided which include markings to aid in modifying the device from a full root replacement to a sub-coronary application. However, these markings are of only marginal assistance to the surgeon. One bioprosthetic stentless aortic root uses very unrefined surface indicators formed by sutures which are sutured through the tissue. Another stentless aortic root requires the surgeon to rely on sketches which are provided in surgical literature.

For other bioprosthetic devices, such as a valved conduit, the device must be oriented and implanted correctly with respect to blood flow direction. Still other bioprosthetic devices, such as pericardial patches, may require that the device be oriented and implanted in a particular manner. For example, it may be desirable to implant the patch so that the strongest axis of the device is aligned with the major stress axis. Other bioprosthetic devices, such as stentless mitral valves or mitral valve repair kits can be scaled (cut down) for a proper fit while maintaining proper geometry. Further, annuloplasty rings must be of the correct size for valve repair.

SUMMARY OF THE INVENTION

Accordingly, it is a general aim of the present invention to provide a new method and apparatus for sculpting a bioprosthetic implant, such as a bioprosthetic root of a stentless aortic valve prosthesis or providing directional indicators or other information to biological prostheses such as a pericardial patch, valved conduit, etc. The prosthesis includes a marking or visual guide for excising portions of the prosthesis or instructions for use of the prosthesis, such as the direction or position of the prosthesis relative to implant position. In one embodiment, a prosthetic stentless aortic tissue valve comprises a substantially annular valve body which includes at least one leaflet or other type of occluder carried therein for occluding blood flow through the valve body. An aortic root extends from the valve body and is generally coaxial with the valve body. A visual marking is provided on the root and provides a sculpting guideline for use by a surgeon during implantation of the prosthetic heart valve to trim the root. The marking indicates portions of sinus areas of the root which are removed to create a sub-coronary prosthetic stentless aortic valve. In one embodiment, the visual marking generally conforms to the leaflet of the bioprosthetic heart valve. The marking may be formed by any appropriate means, including a biocompatible dye or laser markings.

DETAILED DESCRIPTION OF THE PREFERRED EMBODIMENTS

The present invention provides indicators on bioprosthetic devices to aid in their implantation. Such indicators provide a number of advantages. These advantages include that the indicators allow the surgeon to tailor each device to the specific physiology of the patient. The devices can also be used for multiple purposes in that the device may be modified for various applications of the device. Furthermore, such indicators allow the device to be accurately oriented to optimize results of the use of the device. In addition, the indicators do not affect the integrity or durability of the device.

Figure 1:
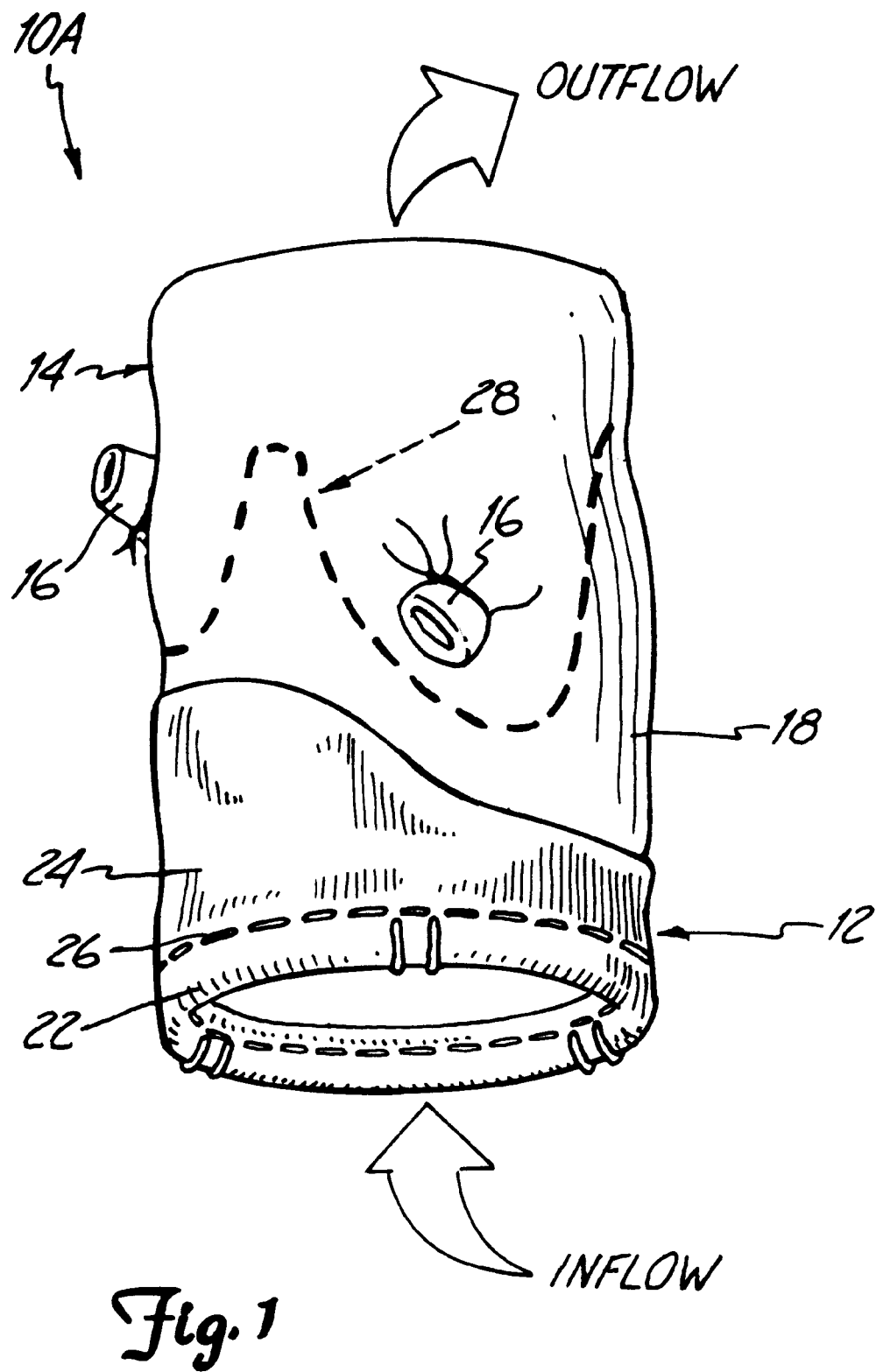
FIG. 1 is a side perspective view of a prosthetic stentless aortic tissue valve in accordance with the present invention.

FIG. 1 is a side perspective view of a bioprosthetic stentless aortic root valve 10A in accordance with the present invention. Valve 10A includes a valve body portion 12 and an aortic root portion 14. Root 14 includes remnant coronary ostia 16. Valve body 12 includes a commissure support portion 18, annular orifice 22, reinforcement material 24 and sutures 26 which attach material 24 to annular orifice 22. Reinforcement material 24 could be, for example, a non-absorbable polymer, such as a polyester, polytetrafluoroethylene, or nylon, pericardium tissue, a resorbable polymer, such as polylactic acid (PLA) or polyglycolic acid (PGA), or a semi-rigid thin stent. Material 24 may also be coupled to root 14 using an adhesive.

As shown in FIG. 1, root valve 10A includes visual marking 28 on root valve 10A which generally divides root 10A into two portions, valve body 12 and root 14. Remnant coronary ostia 16 are carried on the root 14. Visual marking 28 generally conforms to the profile of the leaflets (not shown in FIG. 1) carried within valve body 12.

Valve 10A as shown in FIG. 1 is adapted for replacement of the full natural aortic root of a patient. However, during the surgical operation, if the surgeon discovers that the natural aortic root or aortic arch is healthy, the surgeon may decide to leave the natural root intact and implant a sub-coronary valve replacement within the aortic arch. Typically, a sub-coronary valve will provide enhanced hemodynamics, long term durability and reduced surgical complexity and is therefore preferable to the root version.

Figure 2:
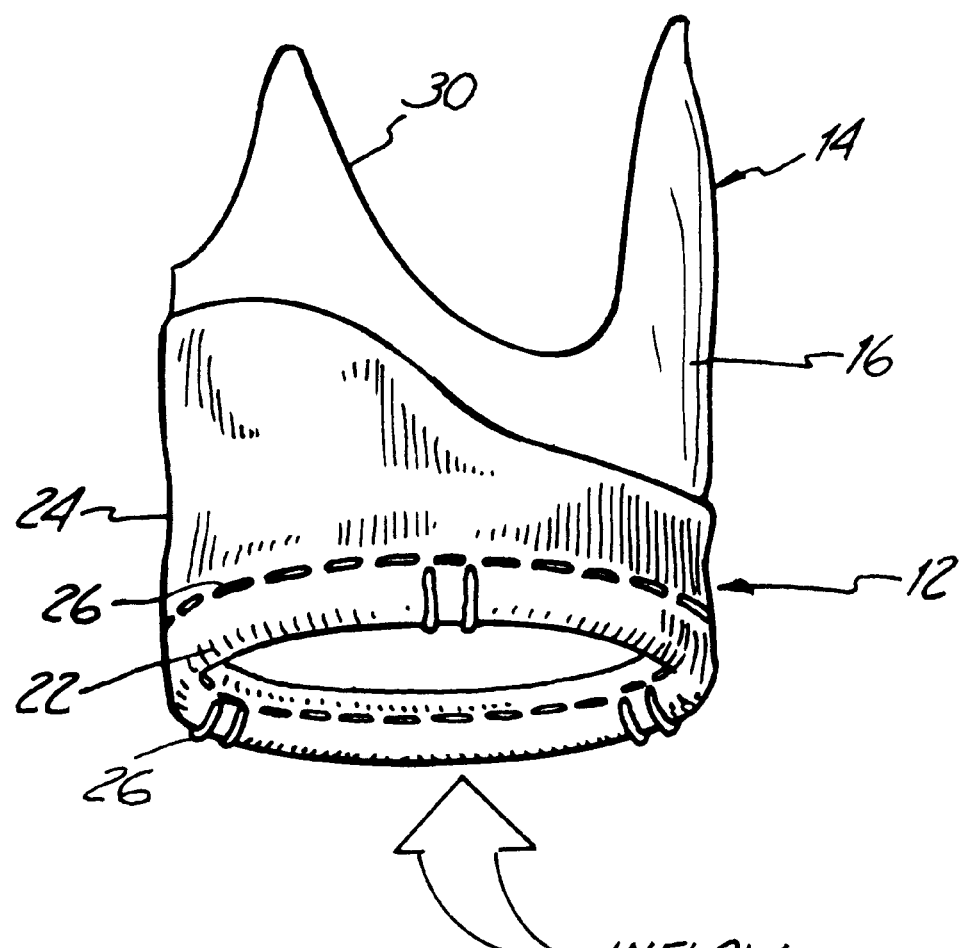
FIG. 2 is a side perspective view of the valve of FIG. 1 following excision of portions of the prosthetic aortic root shown in FIG. 1.

The present invention allows the surgeon to quickly and efficiently modify tissue valve 10A as shown in FIG. 1 by removing root 14 to form sub-coronary tissue valve 10B shown in FIG. 2. The portions 12, 14 for subcoronary implants may be separated immediately prior to implantation, or during the implant procedure if full root is used. As shown in FIG. 2, root 14 has been removed, utilizing standard surgical implements (scissors, scalpels, etc.) at visual marking 28, leaving cut line 30 on the outflow edge of valve 10B. Thus, tissue valve 10B is now adapted for sub-coronary implantation into the natural aortic root of the patient. This modification could be performed on either one, two or three of the coronary sinuses, depending on the surgeon's preferences.

Figure 3:
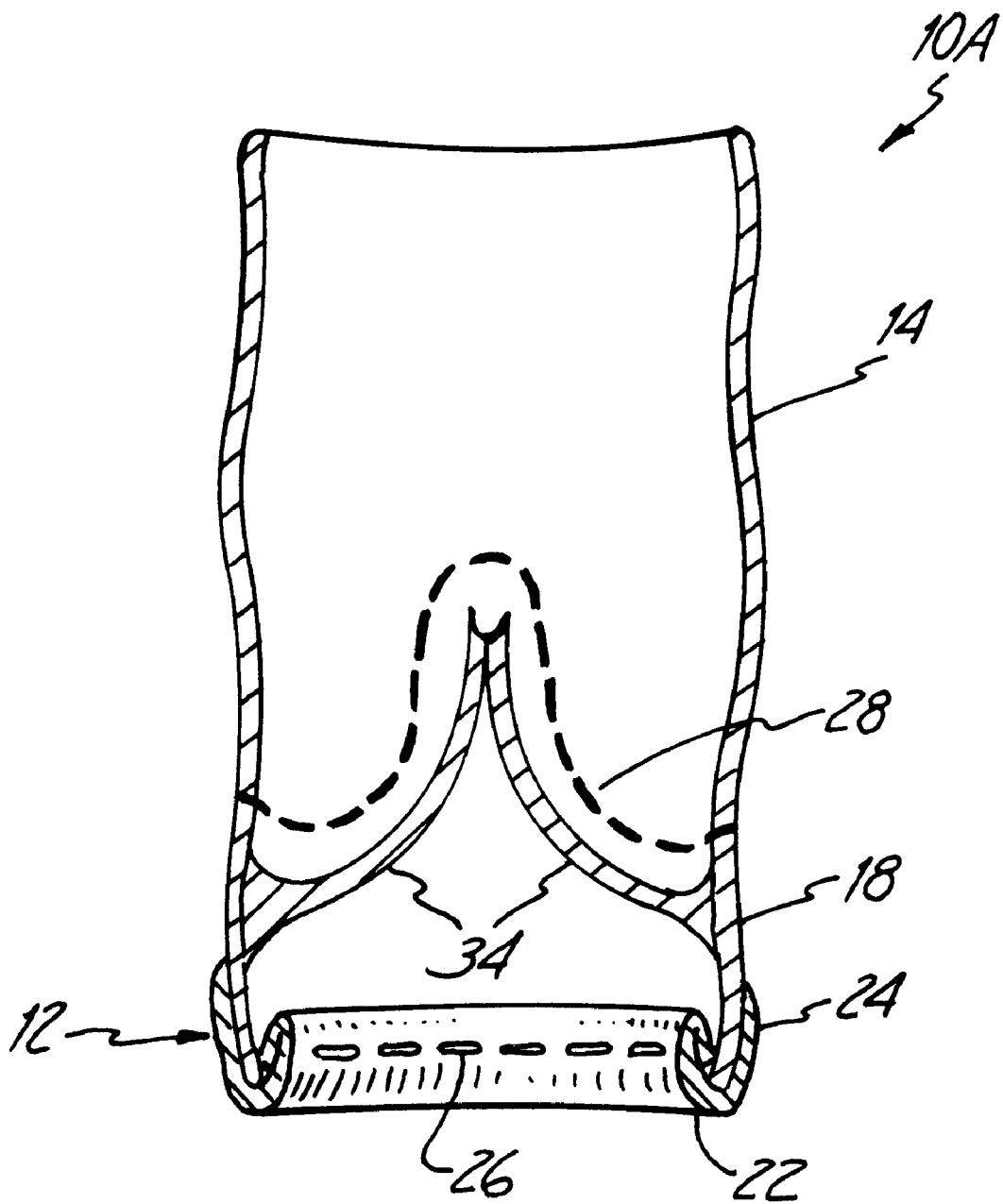
FIG. 3 is a cross-sectional view of the root valve of FIG. 1 showing leaflets carried therein.

Visual marking 28 is preferably formed during manufacture of valve 10A and preferably provides an optimal, or near optimal sculpting indicator for each individual valve. Specifically, visual marking 28 is positioned above and closely follows the shape and contour of leaflets 34 shown in FIG. 3 which are carried in valve body 12. FIG. 3 is a cross-sectional view of valve 10A and shows the relationship between visual marking 28 and leaflets 34. It is important in stentless aortic valves that marking 28 is placed in a consistent fashion in relation to the point of leaflet attachment in order to assure proper valve function. Marking 28 can be formed from any suitable biocompatible material which will be visible by the surgeon during surgery. For example, marking 28 may be formed of toluidine blue dye or other organic biocompatible dyes. In another embodiment, a laser may be used to form visual marking 28. The energy output, wavelength and duration of such laser should be selected such that valve 10A is not damaged during the marking procedure. Preferably, visual marking 28 is applied prior to packaging and shipping of valve 10A. The visual markings of the present invention do not damage the bioprosthesis or affect the functioning of the prosthesis.

Marking 28 may be applied manually by visually inspecting valve body 12 and the position of the leaflets. Further, a template may be used to apply visual marking 28. A machine may also be employed to apply marking 28 in which the machine follows a template stored in a computer memory. Additionally, such machine may include a sensor such as an ultrasonic sensor, a laser indicator, a contact measuring device, MRI, etc., which is capable of locating the position of leaflets within valve 10A and responsively controlling application of marking 28 to enhance the precision of the application of marking 28. In another embodiment, a polymer, which may be colored, such as a fabric, or other visual markers are adhered using biocompatible biological or synthetic adhesives to the surface of the device, or the adhesive itself could be colored, indicating where the tissue should be excised, such as along marking 28 of FIG. 1, or may even include a part of or the entire region between marking 28 and orifice 22.

One aspect of the present invention is that the visual markings do not damage the device. One important concern with bioprosthetic devices is that of mineralization. Mineralization refers to a process in which the material of the device becomes inflexible and brittle due to the incorporation of calcific deposits. Research indicates that one cause of mineralization is abnormal stress concentrations in the tissue. For example, puncturing the surface of the device, such as with sutures, can cause focal stress concentration. Thus, one aspect of the present invention is that the visual markings do not damage the tissue matrix of the device.

Figure 4:
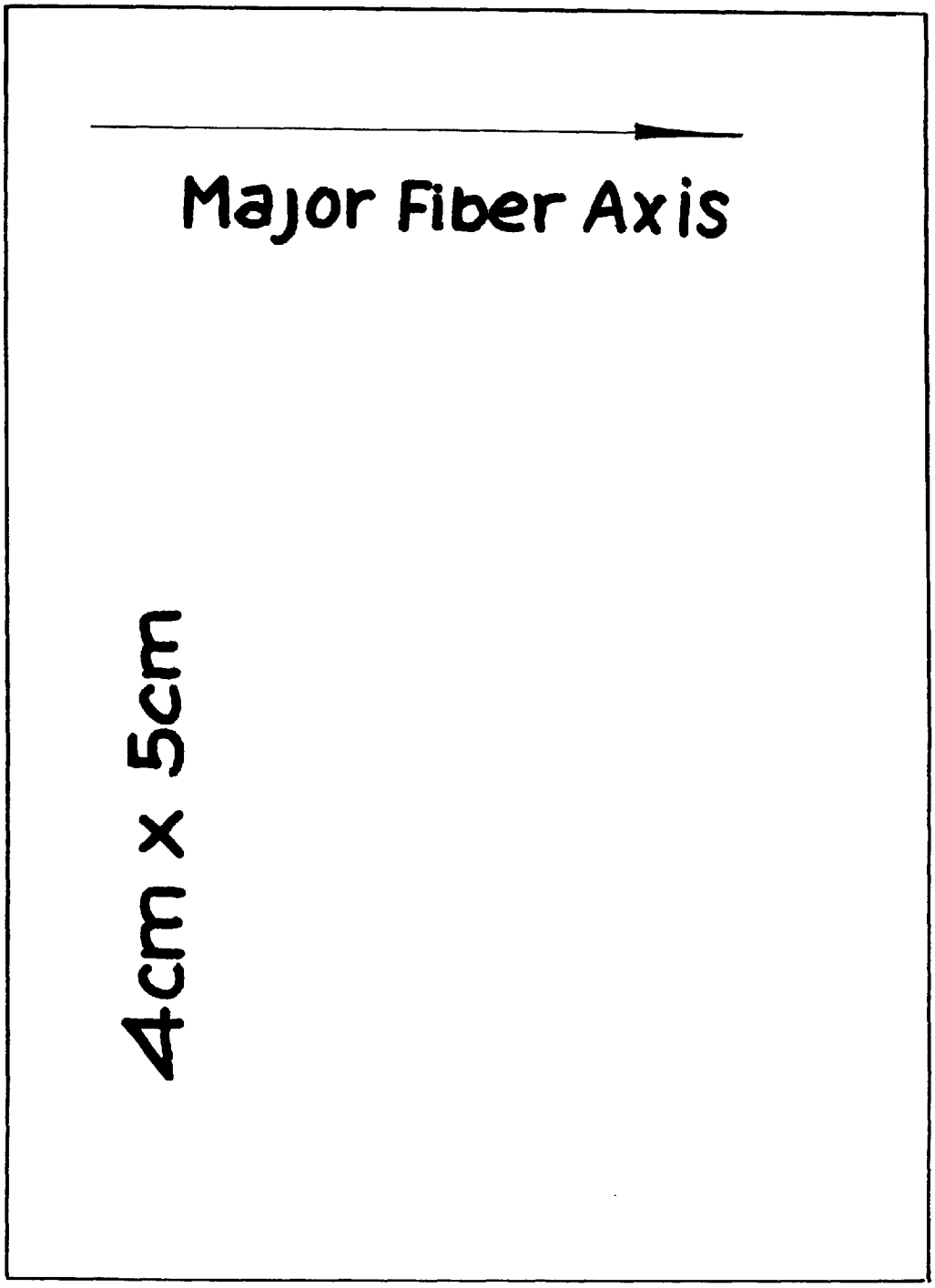
FIG. 4 is a plan view of a pericardial patch in accordance with one embodiment of the invention.

It will be understood that the invention may be used with other types of prostheses. For example, FIG. 4 is a plan view of a pericardial patch 50 in accordance with the invention. The material of patch 50 is typically stronger in the direction of the major fiber orientation. In surgical cases where stress is a factor, it is preferable to use a patch device aligned along the axis of stress. It is within the contemplation of this invention to put a directional indicator, such as an arrow, to indicate the direction of the strong axis of the patch 50, or a written use direction to indicate, for example, which is the smooth or rough side of the patch 50, or the size of the patch 50.

Figure 5:
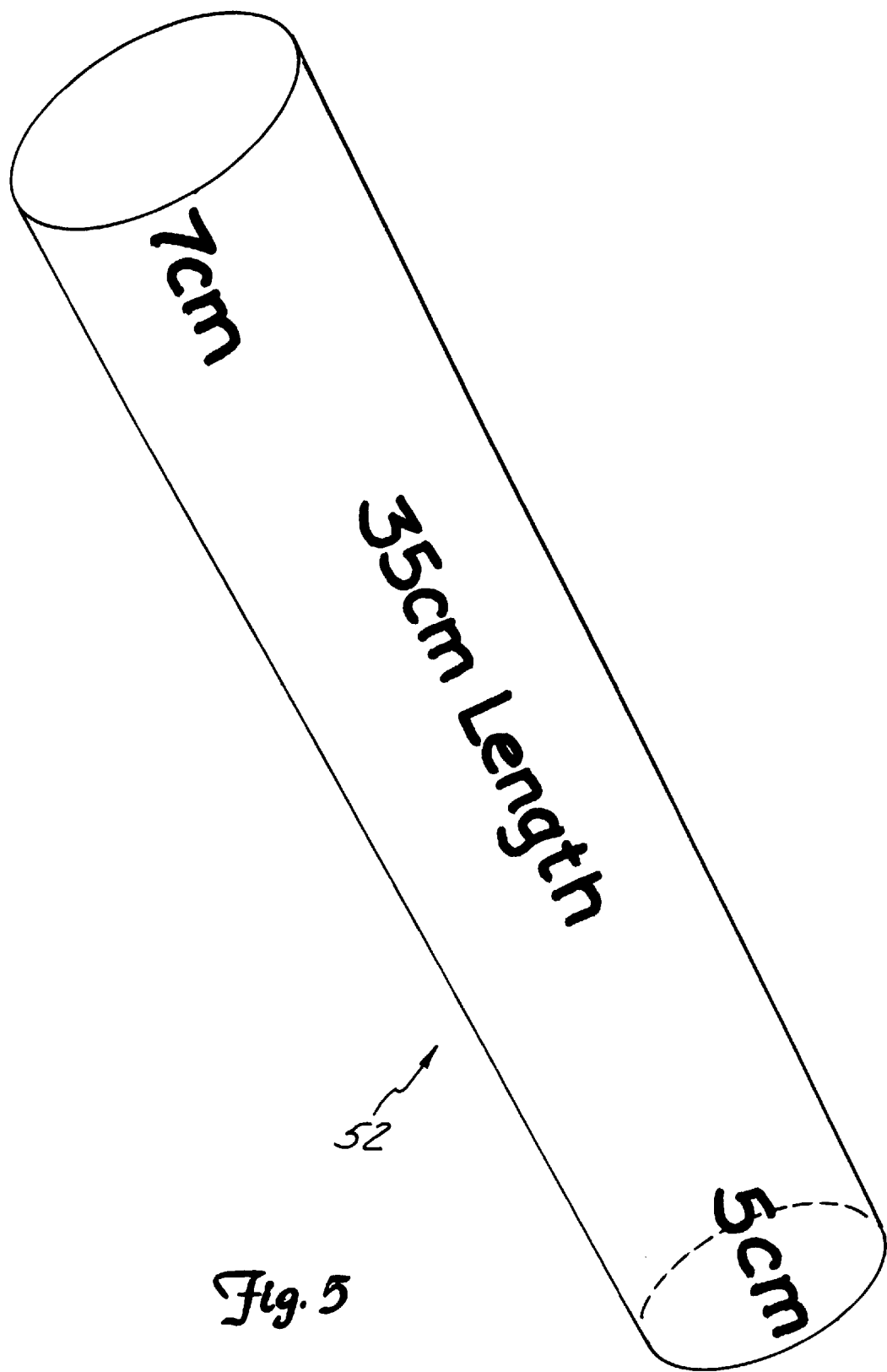
FIG. 5 is a perspective view of a vascular graft or nerve channel in accordance with one embodiment of the invention.
Figure 6:
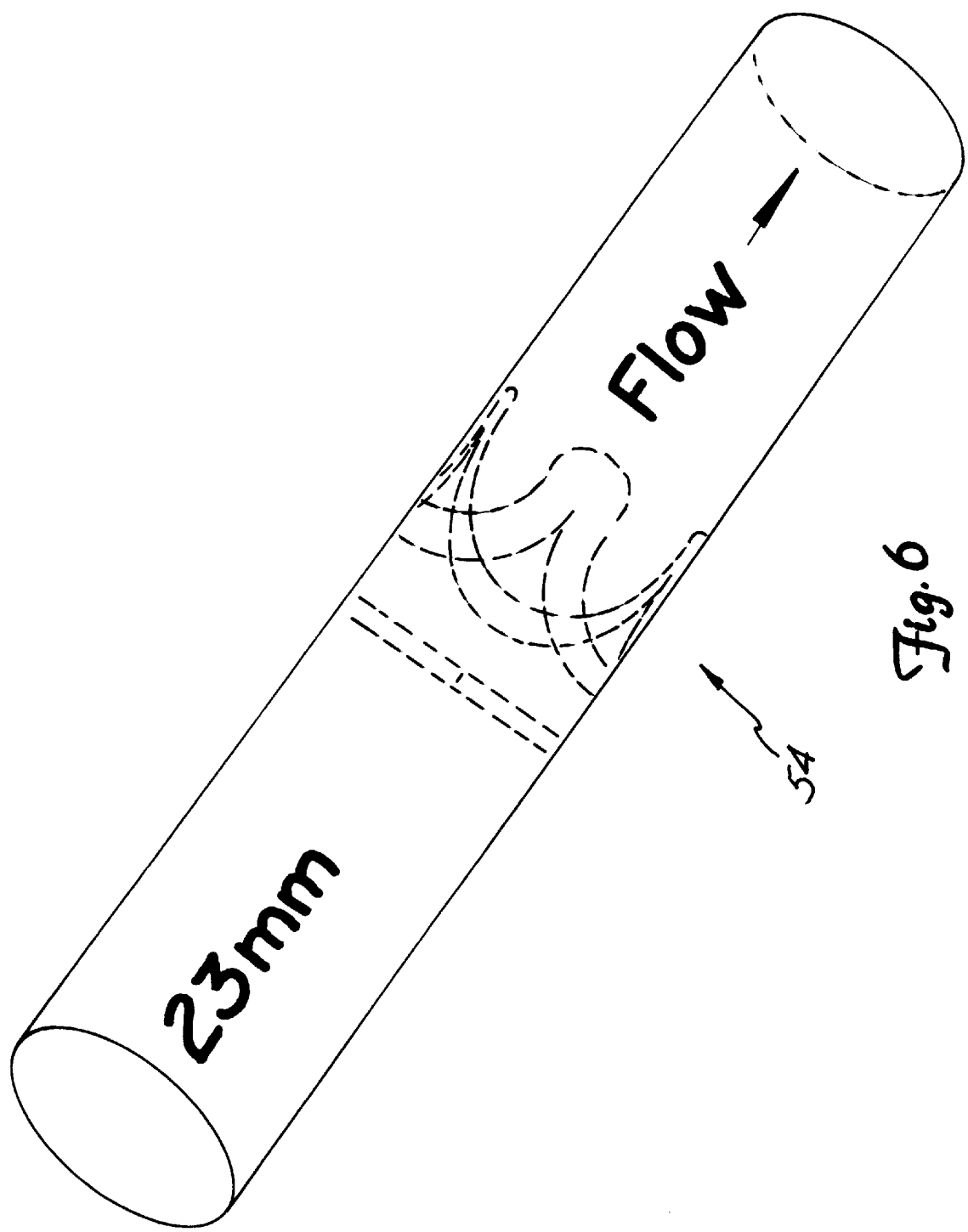
FIG. 6 is a perspective view of a valved conduit in accordance with one embodiment of the invention.

For blood flow conduits comprising a biological or synthetic material, such as a mechanical or biological valved graft 52 shown in FIG. 6 or vascular graft 54 shown in FIG. 5, blood flow directional indicators or size indicators may be placed on the device to assure that the device is oriented and implanted correctly with respect to blood flow direction. This allows the surgeon to identify the distal and proximal end, conduit size, appropriate valve size and position within the conduit, etc. Such markings are preferably applied prior to surgery, preferably during manufacture.

Figure 7:
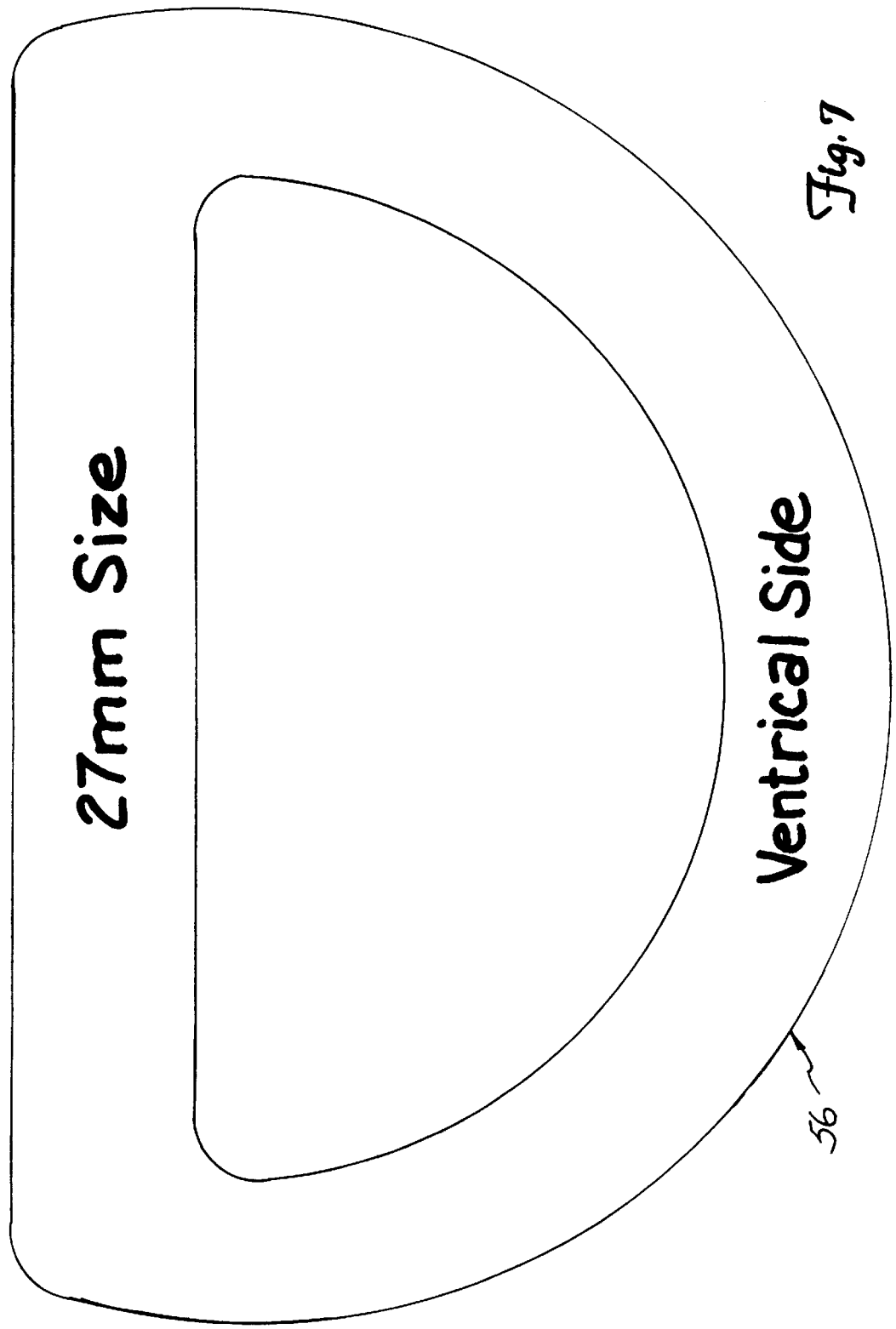
FIG. 7 is a plan view of an annuloplasty ring in accordance with one embodiment of the invention.

An annuloplasty ring 56 shown in FIG. 7, also in accordance with the present invention, provides sizing directions, modification indicators, such as a cut line indicator, and/or placement orientation instructions. This is particularly useful for annuloplasty rings that have variable stiffness around the ring circumferences such as anteriorly or posteriorly or are of designs such that material or geometric properties have importance with regard to implant orientation. For example, in order to improve the healing response of ring 56, cell adhesion proteins may be placed on the surface of the device that contact the mitral annulus.

Figure 8:
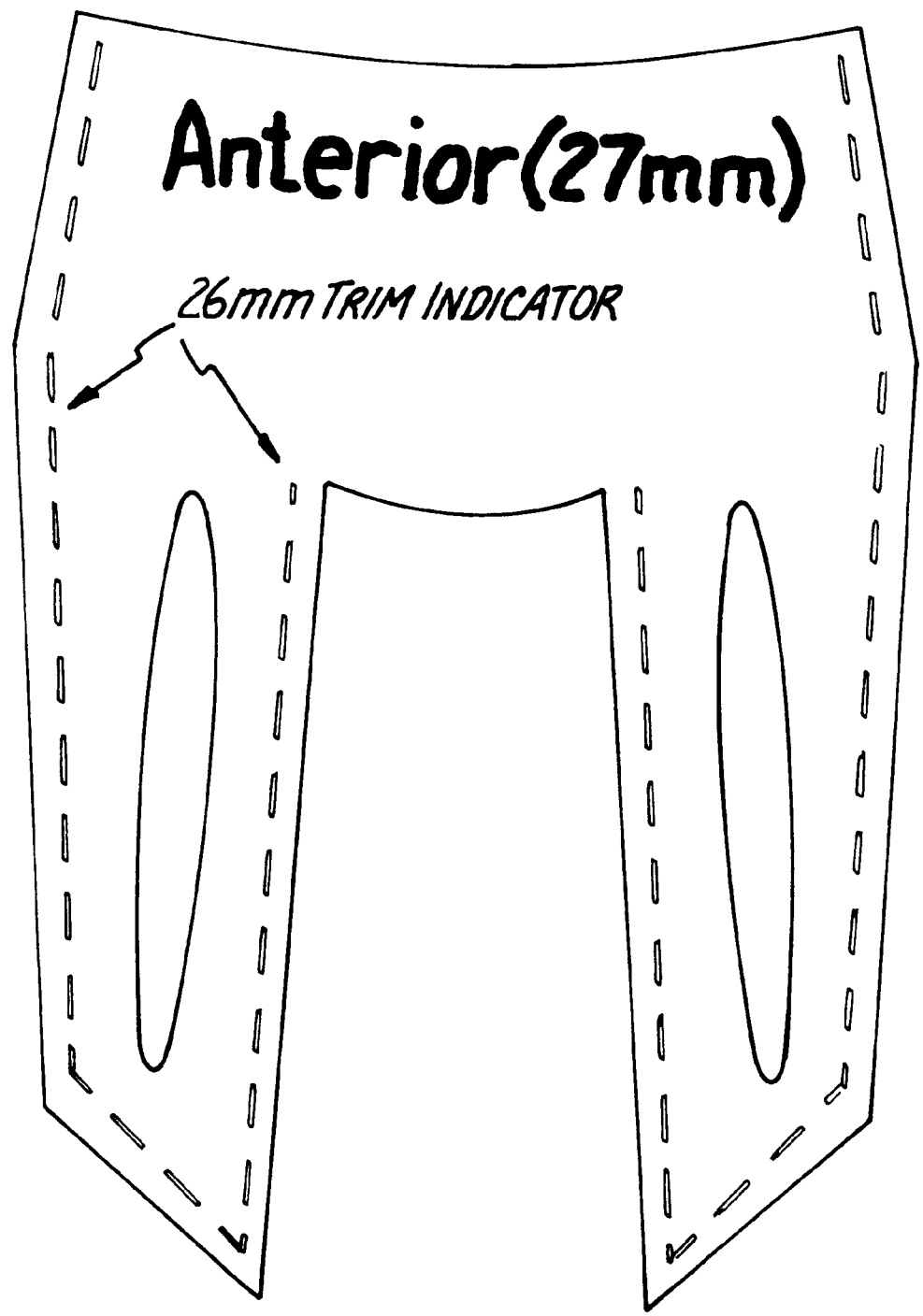
FIG. 8 is a perspective view of an anterior mitral valve repair leaflet or cusp in accordance with one embodiment of the invention.

Additionally, the invention is applicable to stentless mitral valves as well as mitral valve repair kits. Indicators are placed on the valves or individual leaflets as shown in FIG. 8 to allow the surgeon to sculpt the valve proportionately in relation to annulus size for improved valve function. In the case of a full mitral valve replacement, this anterior cusp, shown in FIG. 8, as well as a similar posterior cusp would be combined to form a complete valve. Both of these segments, however, could still be subject to sculpting. This is particularly useful in allowing the surgeon to alter the device with respect to annular geometry as well as length of papillary attachment. In the case of mitral repair kits, each leaflet may have proportional sculpting indicators for the same purpose. This assures that the leaflets are scaled to size with respect to all dimensions and that they are placed in the correct position (anterior or posterior).

Nerve channels may also be made in accordance with the invention where implant orientation and sizing of the nerve channel are important to the success of the device. FIG. 5 is an example of a nerve channel that could be sized appropriately for the intended use, i.e., reduced diameter and length. In addition, ligament replacements could be marked to include sizing information as well as implantation orientation.

As shown and described herein, the invention includes placing indicia on a surface of a prosthetic device. This indicia is applied to a flexible layer of the device, such as shown in the examples set forth herein. The indicia is applied in a manner which does not stress the material to an extent which would damage the material or could lead to mineralization. The indicia is used during the implantation procedure to provide the surgeon or attending staff with information which will aid in the procedure. This simplifies the implantation process. Further, because the information is more readily apparent, the implantation procedure may proceed at a faster rate thereby shortening the length of time needed to perform the surgery. Thus, the invention provides more accurate implantation which requires a shortened surgical procedure.

Although the present invention has been described with reference to preferred embodiments, workers skilled in the art will recognize that changes may be made in form and detail without departing from the spirit and scope of the invention. For example, the visual marking may be formed by any appropriate technique and may comprise a plurality of individual markings or may use color as an indicator. The visual marking is applicable to any bioprosthetic or synthetic replacement or repair device for heart valves or other types of implants.

What is claimed is:

1. A prosthetic stentless aortic valve for replacing a natural aortic heart valve of a patient, comprising:

a substantially annular valve body including a leaflet carried therein for occluding blood flow through the valve body;

an aortic root having an interior surface and an exterior surface spaced from the interior surface, the root including sinus areas and extending generally coaxially from the valve body; and a visual marking carried substantially on the exterior surface of the aortic root providing a sculpting guideline thereon for use during implantation of the prosthetic heart valve to sculpt portions of the sinus areas of the aortic root, wherein the visual marking does not penetrate the interior surface.

2. The prosthetic stentless aortic valve of claim 1 wherein the leaflet extends into the aortic root and the visual marking generally conforms to the leaflet.

3. The prosthetic stentless aortic valve of claim 1 including a plurality of visual markings on the aortic root.

4. The prosthetic stentless aortic valve of claim 1 wherein the visual marking comprises a biocompatible dye applied to the aortic root.

5. The prosthetic stentless aortic valve of claim 1 including a plurality of leaflets.

6. The prosthetic stentless aortic valve of claim 1 wherein the visual marking does not promote mineralization of the tissue matrix.

* * * * *